United States Patent [19]

Zupan et al.

[11] Patent Number: 5,075,295
[45] Date of Patent: Dec. 24, 1991

[54] NOVEL OXYTETRACYCLINE COMPOSITIONS

[75] Inventors: Jacob A. Zupan; Deborah L. Steinbrenner, both of St. Joseph, Mo.

[73] Assignee: Boehringer Ingelheim Animal Health, Inc., St. Joseph, Mo.

[21] Appl. No.: 449,652

[22] Filed: Dec. 12, 1989

[51] Int. Cl.$^5$ .............................................. A61K 31/65
[52] U.S. Cl. ..................................... 514/153; 514/152
[58] Field of Search ................................. 514/152, 153

[56] References Cited

U.S. PATENT DOCUMENTS 4,020,162 4/1977 Ghilardi et al. ...................... 514/153
4,386,083 5/1983 Hacke et al. ......................... 514/152

Primary Examiner—Jerome D. Goldberg
Attorney, Agent, or Firm—David E. Frankhouser; Daniel Reitenbach; Mary-Ellen M. Timbers

[57] ABSTRACT

Novel aqueous oxytetracycline compositions comprising oxytetracycline, polyethylene glycol with a mean molecular weight of 400, and magnesium oxide. These compositions have good clarity and low viscosity.

15 Claims, No Drawings

NOVEL OXYTETRACYCLINE COMPOSITIONS

FIELD OF THE INVENTION

This invention relates to novel aqueous oxytetracycline compositions which comprise oxytetracycline, polyethylene glycol and magnesium oxide.

BACKGROUND OF THE INVENTION

Compositions comprising oxytetracycline are well known. For example, U.S. Pat. No. 3,017,232 describes compositions comprising oxytetracycline salts and polyhydric aliphatic alcohols. U.S. Pat. No. 4,020,162 describes compositions comprising oxytetracycline, magnesium chloride, polyethylene glycol, a base, preservatives, and a buffer system. However, the maximum oxytetracycline concentration which can be achieved in these compositions is only approximately 12% by weight of the total composition.

U.S. Pat. No. 4,386,083 describes compositions comprising oxytetracycline, glycerol formal, and magnesium chloride, magnesium acetate, or magnesium oxide. This composition is described as being able to contain from greater than about 15% by weight to about 35% by weight oxytetracycline.

U.S. Pat. No. 4,081,528 describes an aqueous composition comprising tetracycline, magnesium oxide, and 2-pyrrolidone as a co-solvent.

It is the purpose of this invention to provide an aqueous oxytetracycline composition comprising polyethylene glycol which can contain up to about 30% by weight oxytetracycline, has good clarity and has an acceptable viscosity.

DESCRIPTION OF THE INVENTION

The aqueous oxytetracycline compositions of this invention comprise oxytetracycline, polyethylene glycol, magnesium oxide and water. An effective range of oxytetracycline in the compositions of this invention is generally from about 1% to about 30% by weight of the total composition. Preferably the concentration range of oxytetracycline in the composition is about 10% to about 30% and most preferably, about 15% to about 25%.

The oxytetracycline can be in the form of the free base or a pharmaceutically acceptable acid addition salt such as oxytetracycline hydrochloride.

The molar ratio of magnesium oxide to oxytetracycline is from about 0.80:1 to 1.10:1, preferably from about 0.85:1 to about 1.05:1, and most preferably, from about 0.93:1 to about 0.99:1.

Polyethylene glycol having a mean molecular weight of about 400 is present in the composition of this invention at a concentration of about 15% to about 40%, preferably about 25% to 30%, by weight of the total composition.

The pH range of the composition of the invention is about 8 to about 10, preferably from about 8.1 to about 9.7, and most preferably from about 8.3 to about 9.0. The pH of the composition of this invention can be adjusted, if necessary, by the addition to the composition of an organic base such as monoethanolamine or other pharmaceutically acceptable base.

As an optional ingredient in the compositions of this invention, an antioxidant such as sodium formaldehyde sulfoxylate may be present in a concentration of from about 0.1% to about 1.0% by weight.

The compositions of this invention are preferably prepared by mixing the polyethylene glycol and water at about 60° C. and then sequentially stirring in the magnesium oxide and the oxytetracycline to produce a clear solution. The pH is then adjusted to the desired range. If an antioxidant is to be included in the composition, it is added to the water/polyethylene glycol mixture prior to addition of the magnesium oxide.

The compositions of this invention are useful for topical or parenteral administration of oxytetracycline to animals for veterinary applications.

The compositions have a viscosity such that administration even in cold weather is not a problem. Furthermore these compositions provide effective blood levels of oxytetracycline while producing minimal tissue irritation following intramuscular administration to warm blooded animals.

The following Examples are presented to illustrate the compositions of the present invention.

EXAMPLE 1

The following solution was prepared.

|  | g/500 ml |
|---|---|
| Oxytetracycline (based on a potency of 912 mg/g) | 110.45 |
| Magnesium oxide | 9.15 |
| PEG-400 (polyethylene glycol with a mean molecular weight of 400) | 101.6 |
| Monoethanolamine, to adjust pH to 9.0 | |
| Distilled water to q.s. to | 500 ml |

The PEG-400 was mixed with sufficient distilled water at 60° C. to make approximately 250 ml. The magnesium oxide was added with stirring followed by the addition with stirring of the oxytetracycline. When a clear solution was obtained, the pH was adjusted to 9.0 with monoethanolamine. The solution was then brought up to 500 ml with distilled water.

The final solution so produced contained 20% oxytetracycline, was precipitate-free and had a viscosity of 15 cps.

A comparable solution was prepared when sodium formaldehyde sulfoxylate (final concentration 0.5% weight/volume) was added to the PEG-400/water mixture prior to the addition of magnesium oxide.

EXAMPLE 2

The following solution was prepared using the procedure described in Example 1.

|  | g/500 ml |
|---|---|
| Oxytetracycline (based on a potency of 930.2 mg/g) | 107.8 |
| Magnesium oxide | 9.45 |
| PEG-400 | 125.8 |
| Monoethanolamine, to adjust pH to 9.0 | |
| Distilled water q.s | 500 ml |

The final solution contained 20% oxytetracycline, was precipitate-free and had a viscosity of 18 cps.

EXAMPLE 3

The following solution was prepared using the procedure described in Example 1.

|  | g/500 ml |
|---|---|
| Oxytetracycline (based on a potency of 930.2 mg/g) | 107.9 |
| Magnesium oxide | 9.45 |
| PEG-400 | 200.25 |
| Monoethanolamine to adjust pH to 9.0 | |
| Distilled water q.s. to | 500 ml |

The final solution contained 20% oxytetracycline, was precipitate-free and had a viscosity of 40 cps.

EXAMPLE 4

The following solution was prepared.

|  | g/500 ml |
|---|---|
| Oxytetracycline (based on a potency of 896.2 mg/g | 110.98 |
| Magnesium oxide | 8.75 |
| Sodium formaldehyde sulfoxylate | 2.5 |
| PEG-400 | 150 |
| Monoethanolamine, to adjust pH to 9.4 | |
| Distilled water q.s. to | 500 ml |

The PEG-400 was added to sufficient distilled water at 60° C. to make approximately 250 ml. The sodium formaldehyde sulfoxylate was then added with stirring, followed by addition with stirring of the magnesium oxide. The oxytetracycline was then added with stirring. The temperature of this solution was maintained at 60° C. until a clear solution formed. The solution was then cooled to less than 35° C. and the monoethanolamine (10 ml) was added to adjust the pH of the solution to 9.4. The solution was then brought up to 500 ml with distilled water.

The final solution so produced contained 20% oxytetracycline, was precipitate-free and had a viscosity of 19 cps.

EXAMPLE 5

The following solution was prepared according to the procedure described in Example 1.

|  | g/500 ml |
|---|---|
| Oxytetracycline (based on a potency of 910 mg/g) | 137.4 |
| Magnesium oxide | 11.8 |
| Sodium formaldehyde sulfoxylate | 1.0 |
| PEG-400 | 100 |
| Monoethanolamine, to adjust pH to 9.0 | |
| Distilled water q.s. to | 500 ml |

The final solution contained 250 mg/ml (25%) oxytetracycline, was precipitate-free, and had a viscosity of 34 cps.

EXAMPLE 6

The following solution was prepared according to the procedure described in Example 5.

|  | g/500 ml |
|---|---|
| Oxytetracycline (based on a potency of 910 mg/g) | 137.7 |
| Magnesium oxide | 11.8 |
| Sodium formaldehyde sulfoxylate | 1.0 |
| PEG-400 | 150 |
| Monoethanolamine, to adjust pH to 9.4 | |
| Distilled water q.s. to | 500 ml |

The final solution contained 25% oxytetracycline, was precipitate-free, and had a viscosity of 46 cps.

EXAMPLE 7

The following solution was prepared according to the procedure described in Example 5.

|  | g/500 ml |
|---|---|
| Oxytetracycline (based on a potency of 910 mg/g) | 137.7 |
| Magnesium oxide | 11.8 |
| Sodium formaldehyde sulfoxylate | 1.0 |
| PEG-400 | 125 |
| Monoethanolamine to adjust pH to 9.4 | |
| Distilled water q.s. to | 500 ml |

The final solution contained 25% oxytetracycline, was precipitate-free and had a viscosity of 41 cps.

EXAMPLE 8

The following solution was prepared according to the procedure described in Example 1.

|  | g/500 ml |
|---|---|
| Oxytetracycline (based on a potency of 901 mg/g) | 110.9 |
| Magnesium oxide | 9.4 |
| Sodium formaldehyde sulfoxylate | 1.0 |
| PEG-400 | 150 |
| Monoethanolamine (approx. 17.8 ml) to adjust pH to 9.0 | |
| Distilled water q.s. to | 500 ml |

The final solution contained 20% oxytetracycline, was precipitate-free and had a viscosity of 28 cps.

EXAMPLE 9

The following solution was prepared.

|  | g/500 ml |
|---|---|
| Oxytetracycline hydrochloride (based on a potency of 904 mg/g) | 110.6 |
| Magnesium oxide | 9.15 |
| PEG-400 | 101.8 |
| Monoethanolamine | 16.25 ml |
| Distilled water q.s. to | 500 ml |

PEG-400 was mixed with 175 ml water and magnesium oxide was added. Oxytetracycline hydrochloride was added and the mixture was stirred until a solution was obtained. Monoethanolamine was added very slowly with stirring. When a solution was obtained, the mixture was adjusted to volume with distilled water.

The final solution contained 200 mg/ml (20%) oxytetracycline and was precipitate-free. The pH was 8.7 and the viscosity was 17 cps.

EXAMPLE 10

The following solution was prepared using the procedure described in Example 9.

|                                                          | g/500 ml       |
| -------------------------------------------------------- | -------------- |
| Oxytetracycline hydrochloride                            | 110.8          |
| (based on a potency of 902.8 mg/g)                       |                |
| Magnesium oxide (adjusted to a potency of 16.4%)         | 9.85           |
| PEG-400                                                  | 125.5          |
| Monoethanolamine                                         | to adjust pH   |
| Distilled water q.s. to                                  | 500 ml         |

The final solution contained 200 mg/ml (20%) oxytetracycline, had a pH of 9.0, a viscosity of 26 cps, and was precipitate-free.

EXAMPLE 11

The following solution was prepared according to the procedure described in Example 9.

|                                    | g/500 ml     |
| ---------------------------------- | ------------ |
| Oxytetracycline hydrochloride      | 110.5 g      |
| (based on a potency of 906.5 mg/g) |              |
| Magnesium oxide                    | 9.35         |
| PEG-400                            | 151          |
| Monoethanolamine                   | 16.25 ml     |
| Distilled water q.s. to            | 500 ml       |

The final solution contained 200 mg/ml (20%) oxytetracycline, had a pH of approximately 8.5, a viscosity of 26 cps, and was precipitate-free.

EXAMPLE 12

The following solution was prepared according to the procedure described in Example 9.

|                                  | g/500 ml     |
| -------------------------------- | ------------ |
| Oxytetracycline hydrochloride    | 112.9 g      |
| (based on a potency of 886 mg/g) |              |
| Magnesium oxide                  | 9.33         |
| PEG-400                          | 202          |
| Monoethanolamine                 | 16.25 ml     |
| Distilled water q.s. to          | 500 ml       |

The final solution contained 200 mg/ml (20%) oxytetracycline, had a pH of around 8.5 a viscosity of 55 cps, and was precipitate-free.

COMPARATIVE EXAMPLE A

The following product was prepared using magnesium chloride instead of magnesium oxide.

|                                    | g/500 ml     |
| ---------------------------------- | ------------ |
| Oxytetracycline hydrochloride      | 109.2        |
| (based on a potency of 902.8 mg/g) |              |
| Magnesium chloride hexahydrate     | 50.0         |
| PEG-400                            | 150.5        |
| Sodium formaldehyde sulfoxylate    | 0.99         |
| Monoethanolamine                   | to adjust pH |
| Distilled water q.s. to            | 500 ml       |

PEG-400 was mixed with about 125 ml of distilled water. Sodium formaldehyde sulfoxylate and then magnesium chloride hexahydrate were added with stirring until a solution was obtained. The mixture was kept heated to approximately 60° C. Oxytetracycline hydrochloride was added and the mixture was stirred for 30 minutes. Monoethanolamine was added in order to adjust the pH to between 8.5-9.0. A thick precipitate formed which would not go back into solution before a final pH could be reached.

COMPARATIVE EXAMPLE B

The following product was prepared using magnesium chloride instead of magnesium oxide.

|                                    | g/500 ml     |
| ---------------------------------- | ------------ |
| Oxytetracycline                    | 116.9        |
| (based on a potency of 854.9 mg/g) |              |
| Magnesium chloride hexahydrate     | 50.6         |
| PEG-400                            | 150.4        |
| Sodium formaldehyde sulfoxylate    | 1.0          |
| Monoethanolamine                   | to adjust pH |
| Distilled water q.s. to            | 500 ml       |

PEG-400 was mixed with about 125 ml of distilled water. Sodium formaldehyde sulfoxylate and then magnesium chloride hexahydrate were added with stirring until a solution was obtained. The mixture was kept heated to 50°-60° C. Oxytetracycline was added and the mixture was stirred for one hour. Heating was discontinued and monoethanolamine was added to adjust the pH to between 8.5-9.0. The mixture was filtered and bottled. After several days a precipitate formed which did not go into solution.

What is claimed is:

1. An aqueous oxytetracycline composition comprising:
    a) water
    b) about 1% to about 30% by weight of oxytetracycline in the form of the free base or a pharmaceutically acceptable acid addition salt of oxytetracycline;
    c) about 15% to about 40% by weight of polyethylene glycol having a mean molecular weight of about 400; and
    d) about 0.80:1 to about 1.1:1 molar ratio of magnesium oxide to the oxytetracycline
   wherein the pH of the composition is about 8.0 to about 10.0 and no precipitable is formed.

2. A composition as recited in claim 1 wherein the oxytetracycline is present at a concentration of about 10% to about 30%.

3. A composition as recited in claim 2 wherein the oxytetracycline is present at a concentration of about 15% to about 25%.

4. A composition as recited in claim 1 wherein the polyethylene glycol is present at a concentration of about 25% to about 30%.

5. A composition as recited in claim 2 wherein the polyethylene glycol is present at a concentration of about 25% to about 30%.

6. A composition as recited in claim 1 wherein the molar ratio of magnesium oxide to oxytetracycline is about 0.85:1 to 1.05:1.

7. A composition as recited in claim 6 wherein the molar ratio of magnesium oxide to oxytetracycline is about 0.98:1 to 0.99:1.

8. A composition as recited in claim 1 wherein the pH of the composition is about 8.1 to about 9.7.

9. A composition as recited in claim 8 wherein the pH of the composition is about 8.3 to about 9.0.

10. A composition as recited in claim 1 wherein the oxytetracycline is in the form of oxytetracycline hydrochloride.

11. A composition as recited in claim 1 additionally comprising an antioxidant.

12. An aqueous oxytetracycline composition comprising:
a) water
b) about 15% to about 30% by weight of oxytetracycline in form of the free base or as a pharmaceutically acceptable acid addition salt;
c) about 25% to about 30% by weight of polyethylene glycol having a mean molecular weight of about 400; and
d) about 0.93:1 to about 0.99:1 molar ratio of magnesium oxide to the oxytetracycline,
wherein the pH of the composition is about 8.3 to about 9.0 and no precipitable is formed.

13. A composition as recited in claim 12 additionally comprising an antioxidant.

14. A composition as recited in claim 13 wherein the antioxidant is sodium formaldehyde sulfoxylate.

15. A composition as recited in claim 12 wherein the oxytetracycline is in the form of oxytetracycline hydrochloride.

* * * * *